(12) United States Patent
Steckl et al.

(10) Patent No.: US 10,488,424 B2
(45) Date of Patent: Nov. 26, 2019

(54) DEVICES AND METHODS FOR ANALYZING A BLOOD COAGULATION PROPERTY

(71) Applicant: University Of Cincinnati, Cincinnati, OH (US)

(72) Inventors: Andrew J. Steckl, Cincinnati, OH (US); Giovanni M. Pauletti, Cincinnati, OH (US); Hua Li, Fairfield, OH (US)

(73) Assignee: University of Cincinnati, Cincinnati, OH (US)

( * ) Notice: Subject to any disclaimer, the term of this patent is extended or adjusted under 35 U.S.C. 154(b) by 208 days.

(21) Appl. No.: 15/122,674

(22) PCT Filed: Mar. 3, 2015

(86) PCT No.: PCT/US2015/018487
§ 371 (c)(1),
(2) Date: Aug. 31, 2016

(87) PCT Pub. No.: WO2015/134497
PCT Pub. Date: Sep. 11, 2015

(65) Prior Publication Data
US 2017/0074893 A1    Mar. 16, 2017

Related U.S. Application Data

(60) Provisional application No. 61/947,170, filed on Mar. 3, 2014.

(51) Int. Cl.
*G01N 33/00* (2006.01)
*G01N 33/86* (2006.01)
(Continued)

(52) U.S. Cl.
CPC ......... *G01N 33/86* (2013.01); *G01N 33/4905* (2013.01); *B01L 3/5023* (2013.01);
(Continued)

(58) Field of Classification Search
CPC ........................................ G01N 33/86
(Continued)

(56) References Cited

U.S. PATENT DOCUMENTS

| 5,601,995 A | 2/1997 | Exner |
| 5,939,331 A | 8/1999 | Burd et al. |

(Continued)

FOREIGN PATENT DOCUMENTS

| FR | 2721714 A1 | 12/1995 | |
| WO | WO-9600395 A1 * | 1/1996 | ............... C12Q 1/56 |

OTHER PUBLICATIONS

International Searching Authority, European Patent Office, International Search Report and Written Opinion issued in corresponding PCT Application No. PCT/US2015/018487. dated May 20, 2015 (12 pages).

(Continued)

*Primary Examiner* — Christopher Adam Hixson
*Assistant Examiner* — Emily R. Berkeley
(74) *Attorney, Agent, or Firm* — Wood Herron & Evans LLP (57) ABSTRACT

A device (10) and method for analyzing blood coagulation in a blood sample. The device (10) includes a housing (12) having an analytical membrane (14) partially enclosed in a housing. The analytical membrane (14) includes a porous hydrophilic sample portion (34), a porous hydrophilic analytical portion (36), and a porous hydrophilic wicking portion (38). The porosity of the analytical portion (36) differs from the porosity of the sample portion (34). The method utilizes the device to analyze blood coagulation in a whole blood sample from the distance travelled by the red blood cell leading edge (50) in a predetermined period of time.

26 Claims, 8 Drawing Sheets

(51) Int. Cl.
*G01N 33/49* (2006.01)
*B01L 3/00* (2006.01)

(52) U.S. Cl.
CPC . *B01L 2300/161* (2013.01); *B01L 2400/0406* (2013.01); *Y10T 436/2575* (2015.01)

(58) Field of Classification Search
USPC .......................................................... 436/69
See application file for complete search history.

(56) References Cited

U.S. PATENT DOCUMENTS

| 8,089,013 | B2 | 1/2012 | Steckl et al. |
| 2012/0107851 | A1 | 5/2012 | Killard et al. |
| 2012/0207851 | A1 | 8/2012 | Martin |
| 2013/0215492 | A1 | 8/2013 | Steckl et al. |

OTHER PUBLICATIONS

D. Y. Kim and A. J. Steckl, "Liquid-State Field-Effect Transistors Using Electrowetting", Appl. Phys. Lett.90 (3), 043507, 2007.

D. Y. Kim and A. J. Steckl, "Electrowetting on Paper for Electronic Paper Display", ACS Applied Materials and Interfaces,2, pp. 3318-3323, 2010.

S. Purandare, E. F. Gomez and A. J. Steckl, "High brightness phosphorescent organic light emitting diodes on transparent and flexible cellulose films", IOP Nanotechnology, 25 (9), 094012, Mar. 2014.

H. Li, D. Han, G. Pauletti, and A. J. Steckl, "Blood coagulation screening using a paper-based microfluidic later flow device", Lab-Chip, 14, 4035, Sep. 2014.

A. W. Martinez, S. T. Phillips, M. J. Batte and G. M. Whitesides, "Patterned Paper as a Platform for Inexpensive, Low-Volume, Portable Bioassays", Angew. Chem. Int. Ed. 46, 1318, 2007.

X. Li, D. Ballinni, and W. Shen, "A perspective on Paper-Based Microfluidics: Current Status and Future Trends", Biomicrofluidics6, 011301, 2012.

A. J. Steckl, "Circuits on Cellulose", IEEE Spectrum, 48-52, Feb. 2013.

K. P. Cabral, J. Ansell, "Oral direct factor Xa inhibitors for stroke prevention in atrial fibrillation", Nature Reviews Cardiolology9, 385, 2012.doi: 10.1038/nrcardio.2012.19.

T. S. Potpara, G. Y. Lip, S. Apostolakis, "New anticoagulant treatments to protect against stroke in atrial fibrillation", Heart, 2012.doi: 10.1136/heartjnl-2012-301841.

P. B. Berger, "Assessment of advantages and disadvantages of agents used for therapeutic anticoagulation", Disease-a-Month, 58, 462, 2012.

D. J. Perry, D. A. Fitzmaurice, S. Kitchen, I. J. Mackie, S. Mallet. "Point-of-care testing in haemostasis", British Journal of Haematol. ,150, 501, 2010.

T. D. Christensen and T. B. Larsen, "Precision and accuracy of point-of-care testing coagulometers used for self-testing and self-management of oral anticoagulation therapy", Journal of Thrombosis and Haemostasis, 10, 251, 2012. doi: 10.1111/j.1538-7836.2011.04568.x.

\* cited by examiner

DEVICES AND METHODS FOR ANALYZING A BLOOD COAGULATION PROPERTY

RELATED APPLICATION

The Present application claims priority to U.S. Ser. No. 61/947,170 filed Mar. 3, 2014, the disclosure of which is hereby incorporated herein by reference in its entirety.

FIELD

The present invention is directed to devices and methods for analyzing a blood property and more particularly to devices and methods for analyzing a blood coagulation utilizing an analytical membrane.

BACKGROUND

Cardiovascular disease is the largest cause of death worldwide. Coagulation, the process by which blood forms clots, involves a cascade of interactions between blood platelets and various coagulation factors. Physiologically, blood coagulation serves to control blood loss from a damaged vessel. In many patients, however, inhibition of blood coagulation using blood-thinning medication (anticoagulants) such as warfarin is required to reduce the risk for stroke, pulmonary embolism, heart attack, and other life-threatening cardiovascular diseases. Constant monitoring of long-term anticoagulation efficacy is critical for these patients. If the anticoagulant drug level is too low, the risk of blood clot formation is high, if the drug level is too high, severe bleeding (hemorrhage) can occur. Traditionally, oral anticoagulation therapy (OAT) is monitored by quantifying the prothrombin time expressed in international normalized ratios (INRs). These measurements are usually performed by trained specialists in a hospital or laboratory setting that meets the federal regulatory requirements.

Point of care (POC) testing devices that can be used in a caregiver's office or at home by properly selected and trained patients or their caregivers can reduce costs and improve patient outcomes. For example, this approach may provide increased convenience for the patient, rapid test results, frequent monitoring of anticoagulation efficacy to reduce the risk of bleeding or thrombotic complications (even if the patient is traveling for extended periods or is located in areas with a low density of healthcare facilities), and overall reduced cost of care.

Existing portable coagulation monitoring devices require access to a power source in order to allow reading of test results and are quite expensive, in the $1-2 k range, making them beyond the reach of a large segment of the population. Low-cost blood coagulation diagnostic testing devices and methods are needed.

SUMMARY

Described herein is a very low cost POC screening device and method that can be used to evaluate a blood property, such as coagulation to provide an indication as to whether the blood coagulation property is within a desired range. In an embodiment, the basic approach utilizes the flow of whole blood through an analytical membrane and works on the principle that as blood clots, the forming network will decrease the ability of red blood cells to flow through the analytical membrane over a set duration of time decreases. The result is, blood that clots slowly will travel a greater distance through the analytical membrane in a set period of time than blood that clots more quickly. Without being bound to any particular biochemical activator of the coagulation cascade, as blood clots, time-dependent formation of the fibrin mesh network in coagulated blood restricts the flow of red blood cells through the porous structure of the analytical membrane. Accordingly, an aspect of the invention is directed to a device having an analytical membrane for analyzing a blood clotting property of a sample. The device may include a housing for the analytical membrane wherein the housing includes a sample reservoir and an observation window. The analytical membrane may have a sample portion, an analytical portion, and a wicking portion and may be formed from one or more overlapping membrane sections having the desired characteristics for each portion.

Various additional objectives, advantages, and features of the invention will be appreciated from a review of the following detailed description of the illustrative embodiments taken in conjunction with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description given below serve to explain the invention.

DETAILED DESCRIPTION

Figure 1:
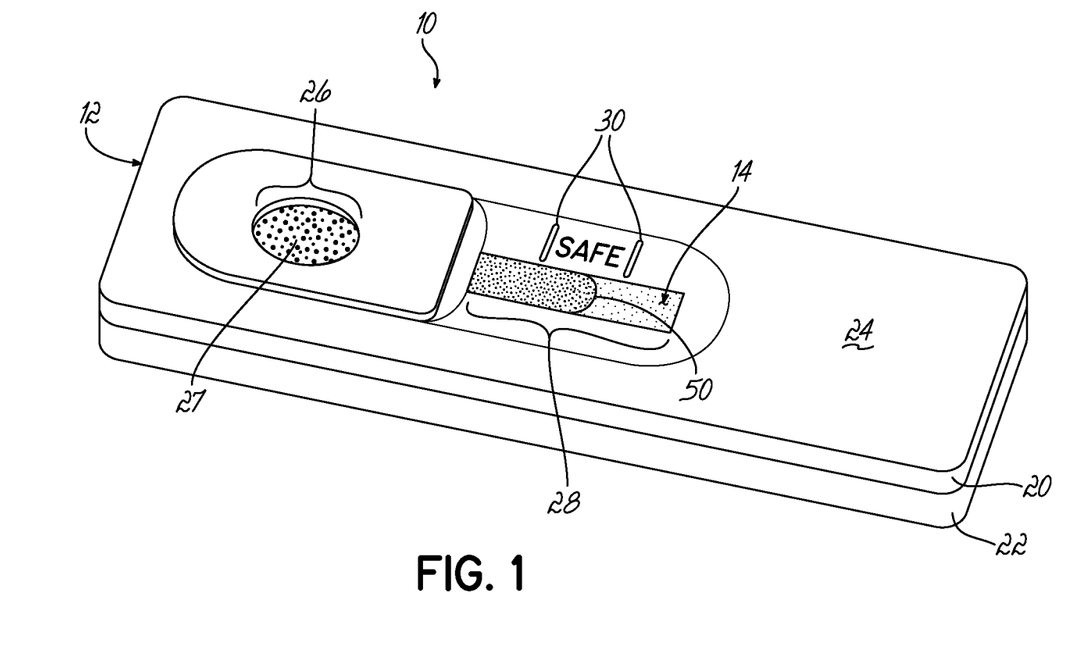
FIG. 1 is a perspective view of a blood property analytical device in accordance with embodiments of the invention.
Figure 2:
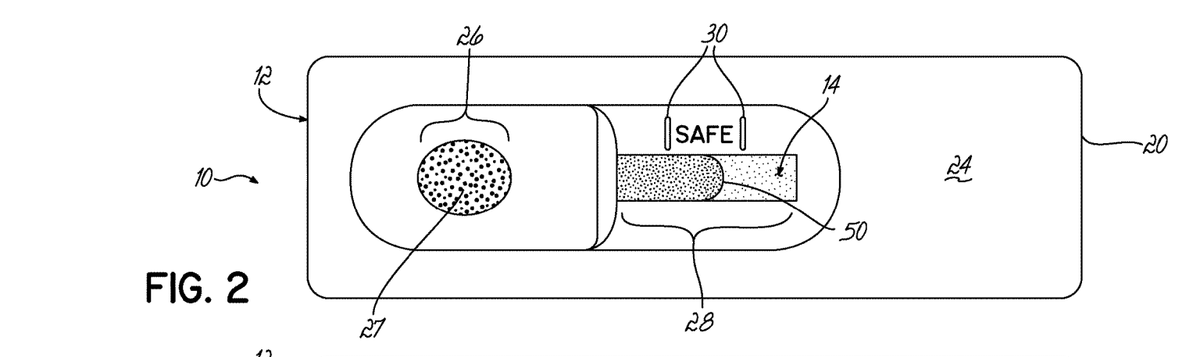
FIG. 2 is a top view of the device of FIG. 1.
Figure 2A:
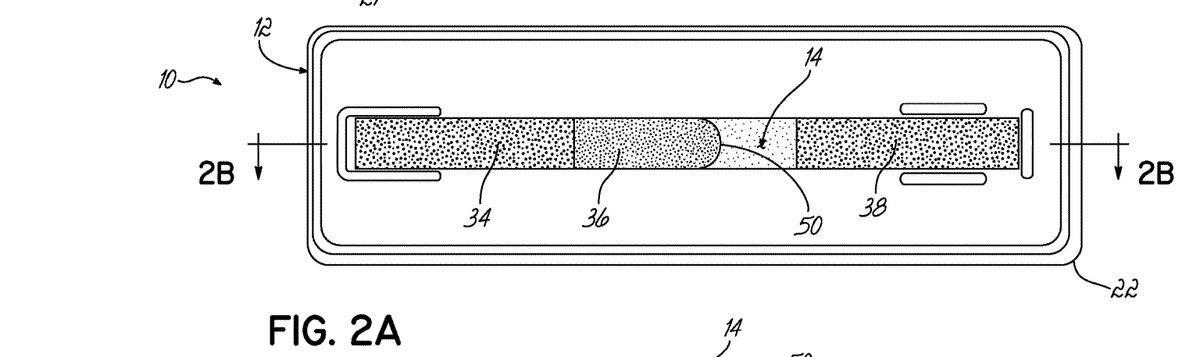
FIG. 2A is a dissembled top view of the device of FIG. 2 with the top cover of the cassette removed.
Figure 2B:
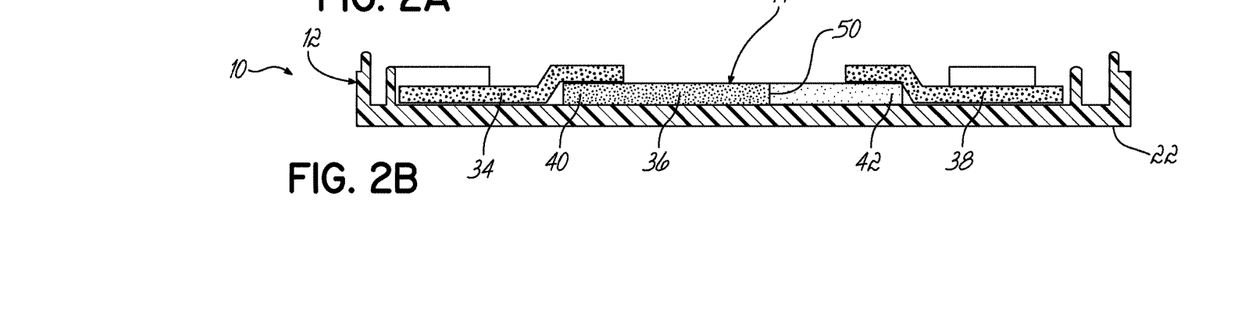
FIG. 2B is longitudinal cross-section side view of the device of FIG. 2A taken along lines 3-3.

With reference to FIGS. 1 to 2B, an embodiment of the invention is directed to an analytical device 10 for analyzing a blood coagulation property (also referred to herein as a blood clotting property) having a housing 12 and an analytical membrane 14.

The housing 12 provides structural support for the analytical membrane 14 and, as illustrated in FIGS. 2 and 2A, may have an upper portion 20 and a lower portion 22. In the exemplary embodiment, the upper portion 20 of the housing 12 has an upper surface with a sample window 26 configured to receive a liquid sample and to convey the sample to the analytical membrane 14. The housing 12 also includes an observation window 28 that allows for observation of the analytical membrane 14. The housing 12 may further include additional markings 30 adjacent the observation window 28 to indicate the results of the analysis. For example, the markings 30 may indicate that the blood clotting property is within or outside (high or low) of a normal or safe range. The lower portion 22 of the housing 12 provides support to the lower surfaces of the analytical membrane 14. Additionally, positioning the upper portion 20 of the housing 12 over the lower portion 22 of the housing 12 maintains the position of the analytical membrane 14 in the device 10.

The analytical membrane 14 includes at least an analytical portion and, in some embodiments, also includes a sample receiving portion, a wicking portion, or both a sample receiving portion and a wicking portion. Generally, the sample receiving portion is located proximal to the analytical portion and the wicking portion is located distal to the analytical portion. In an embodiment, the sample receiving, analytical, and wicking portions are all formed from a single length of porous membrane material. In the embodiment illustrated in FIGS. 2A and 2B, the analytical membrane 14 is formed from three membrane sections: a sample section 34, which corresponds with the sample receiving portion, an analytical section 36, which corresponds with the analytical portion, and a wicking section 38, which corresponds with the wicking portion. The sample section 34 is in contact with and overlaps a proximal end 40 of the analytical section 36 and the wicking section 38 is in contact with and overlaps a distal end 42 of the analytical section 36. Some embodiments may lack either a sample section or a wicking section. Embodiments of the analytical membrane 14 are capable of analyzing the blood coagulation property without any additional reagents or pretreatments.

The sample section 34 functions to absorb the sample fluid volume from the reservoir 26 in the housing 12 and then to release the sample fluid volume into the analytical section 36. To perform this function, the sample section 34 has a high porosity. In an embodiment, the porosity of the sample section 34 is at least about 90% or alternatively, the porosity is in a range from about 92% to about 97%. Another feature of the sample section 34 is that the pore size in the membrane must be large enough for red blood cells to easily pass through the sample section 34 and into the analytical section 36. In an embodiment, the pore size in the sample section 34 ranges from about 50 μm to about 150 μm. Embodiments of the sample section 34 may have a thickness that ranges from about 200 μm to about 500 μm, and alternatively, from about 350 μm to about 450 μm. Additionally, in some embodiments, sample section 34 is formed from a material that tends to not retain or damage biological structures like cells, or significantly interact with proteins and other biological components in a sample volume. The sample section 34 may be formed from hydrophilic materials having the above-identified characteristics. In an exemplary embodiment, the sample section 34 is a fiberglass membrane, such as the fiberglass membrane marketed under the trade name Millipore G041 having a porosity of about 93%. Alternatively, the sample section 34 may be formed from polyester materials. The thickness of the Millipore G041 fiberglass membrane is about 430 μm.

The analytical section 36 utilizes a combination of pore size, porosity, and the resulting flow rate to provide a desired flow of blood cells and resistance to the flow of clotting blood to allow for analysis of the sample. The combination of these characteristics results in red blood cells being separated from plasma at a reasonable speed as the sample flows though the analytical membrane 14. In an embodiment, the pore size in the analytical section 36 ranges from about 2.5 μm to about 30 μm or alternatively, the pore size is about 5 μm. In an embodiment, the porosity of the sample section 34 ranges from about 70% to about 90% or alternatively, the porosity is in a range from about 75% to about 80%. The flow rate ranges from about 0.1 mm/s to about 1 mm/s or alternatively, the flow rate is in a range from about 0.4 mm/s to about 0.6 mm/s, or alternatively, the flow rate is in a range from about 0.5 mm/s to about 0.55 mm/s. Embodiments of the analytical section 36 may have a thickness that ranges from about 100 μm to about 250 μm, and alternatively, from about 120 μm to about 175 μm.

The analytical section 36 may be formed from hydrophilic material having the above described characteristics as well as having high protein-binding affinity and a light color for good visual contrast with red blood cells. The analytical membrane 14 may optionally include a non-porous backing material on which the porous membrane material is formed. In an exemplary embodiment, the analytical section 36 is a nitrocellulose membrane, such as the nitrocellulose membrane marketed under the trade name Millipore HF075 having a porosity of about 78%, a flow rate for water of about 0.5 mm/s and a pore size that ranges from about 3 μm to about 20 μm. The thickness of the unbacked portion of the Millipore HF075 nitrocellulose membrane is about 135 μm and about 185 μm with a 2 mil backing and about 235 μm with a 4 mil backing.

The wicking section 38 absorbs liquid in the sample to provide continuous capillary force to drive fluid flow from the sample section 34 through the analytical section 36 and into the wicking section 38. In an embodiment, the wicking section 38 is capable of absorbing at least the volume of the sample, and alternatively, a liquid volume that is greater than the sample before becoming saturated. Embodiments of the wicking section 38 may have a thickness that ranges from about 250 μm to about 850 μm, and alternatively, from about 400 μm to about 550 μm. In an embodiment, the wicking section 38 is formed from a cellulose material, such as an absorbent cellulose paper marketed under the trade name Millipore C048 having a flow rate of about 0.63 mm/s and porosity of about 72%. The thickness of the Millipore C048 cellulose paper is about 480 μm.

Embodiments of the device 10 may be capable of analyzing a variety of desired sample volumes such as from about 15 μL to about 150 μL and alternatively in a range from about 20 μL to about 60 μL or about 25 μL to about 50 μL. It will be appreciated that the dimensions of the housing 12 and the dimensions of the analytical membrane 14 will vary to accommodate the desired sample volume. In an embodiment, the device 10 is capable of analyzing a sample having volume of about 30 μL. In this exemplary embodiment, the sample section 34 has a length of about 13 mm and a width of about 3 mm. The analytical membrane 14 has a length of about 30 mm and a width of about 3 mm and the wicking section 38 has a length of about 20 mm and a width of about 3 mm. The sample section 34 overlaps the proximal end 40 of the analytical section 36 by about 8 mm and the wicking section 38 overlaps a distal end 42 of the analytical section 36 by about 2 mm. In another embodiment, the device 10 is capable of analyzing a larger volume, such as about 70 μL to about 80 μL. In this embodiment, the sample section 34 has a length of about 20 mm and a width of about 4 mm. The analytical membrane 14 has a length of about 25 mm and a width of about 4 mm and the wicking section 38 has a length of about 20 mm and a width of about 4 mm. The sample section 34 overlaps the proximal end 40 of the analytical section 36 by about 2.5 mm and the wicking section 38 overlaps a distal end 42 of the analytical section 36 by about 2.5 mm.

In embodiments in which analytical section 36 includes a non-porous backing, the overlapping sample section 34 and wicking section 38 will contact the upper surface of the analytical membrane 14. If the analytical section 36 does not include a non-porous backing, then the overlapping sample and wicking section 38s may contact either the upper surface or lower surface of the analytical section 36. Contact between the overlapping portions of the sections is typically maintained with pressure such as applied between the upper and lower sections of the housing 12. Adhesives and other such materials are not typically necessary to maintain contact between the overlapping sections.

During use, a sample of blood is obtained from a subject, such as in a capillary tube after a finger prick. The blood sample is immediately placed in the sample window 26 of the device 10 and the sample is allowed to flow through the analytical membrane 14 for a predetermined duration. After the expiration of the predetermined duration, the relative location of the leading edge 50 of the red blood cells in the samples is identified and correlated to the blood clotting property. The leading edge 50 of the red blood cells is easily identified as the most distal point on the analytical membrane 14 at which red blood cells can be visualized against the background color of the analytical membrane 14. The leading edge 50 will typically appear as a generally well defined red edge that may be slightly curved. If the sample is allowed to flow through the analytical membrane 14 for too great of a time or distance, the leading edge 50 of the red blood cells will become deformed and less sharp. In an embodiment, the sample is allowed to flow through the analytical membrane 14 until the leading edge 50 of the red blood cells has travelled about 10 mm to about 50 mm and alternatively, from about 10 mm to about 20 mm.

The duration of time during which the blood sample is allowed to progress through the analytical membrane 14 is based in part on a desire for the analysis to be completed in a short period of time to make it more easily applied in a point-of-care setting, and also to allow enough time for the formation of the fibrin mesh in the analytical membrane 14 to trap and slow down red blood cell progression through the membrane. Embodiments of the method utilize a duration that ranges from about 1 min to about 10 min and alternatively, from about 2 minutes to about 5 minutes, and further alternatively, about 4 minutes.

Figure 4:
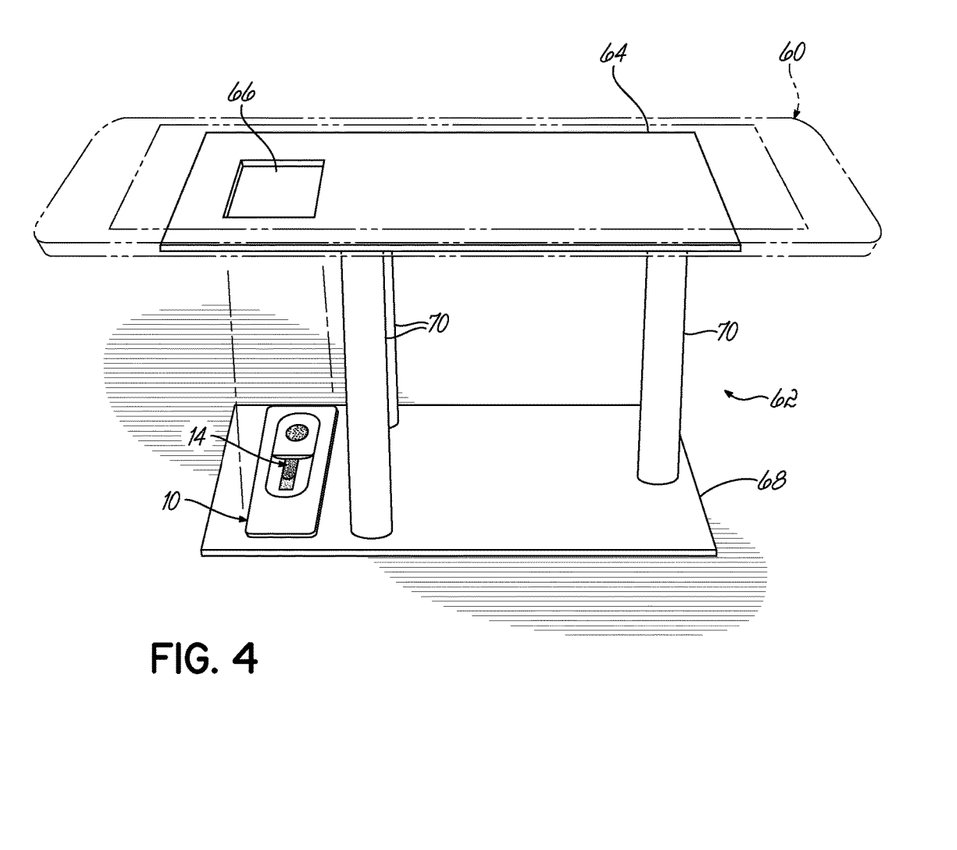
FIG. 4 is a perspective view of a stand for use with embodiments of the blood property analytical device in accordance with embodiments of the invention.

In an embodiment, an image of the analytical membrane 14 is captured, such as with a camera in a mobile device 60 like a mobile phone or tablet. The image may be stored for future reference or evaluated to complete the analysis. FIG. 4 illustrates a stand 62 that may be used with a mobile device 60 to hold the analytical membrane 14 in the field of view of the mobile device 60 at a known distance from the mobile device 60. The exemplary stand 62 has an upper support 64 configured to hold the mobile device 60 at a height of about 10 cm above the analytical membrane 14. The upper support 64 includes an opening 66 through which the camera on the mobile device 60 captures images of the analytical membrane 14. The exemplary stand also includes a lower support 68 on which the analytical membrane 14 is placed, as well as three columns 70 separating the upper support 64 from the lower support 68.

The mobile device 60 may include a software code that captures an image of the analytical membrane 14 at one or more predetermined time points. The software code may also perform one or more of the following functions: identify the red blood cell leading edge, calculate the distance travelled by the red blood cell leading edge, compare the distance travelled against stored data to make a determination if the distance travelled indicates a safe or unsafe condition with respect to the blood clotting property, correlate the distance travelled into an equivalent value such as a partial thromboplastin time (PTT), forward the image and/or distance travelled data to a health care provider, and alert the user and/or a health care provider if the distance travelled indicates an unsafe condition.

Figure 3:
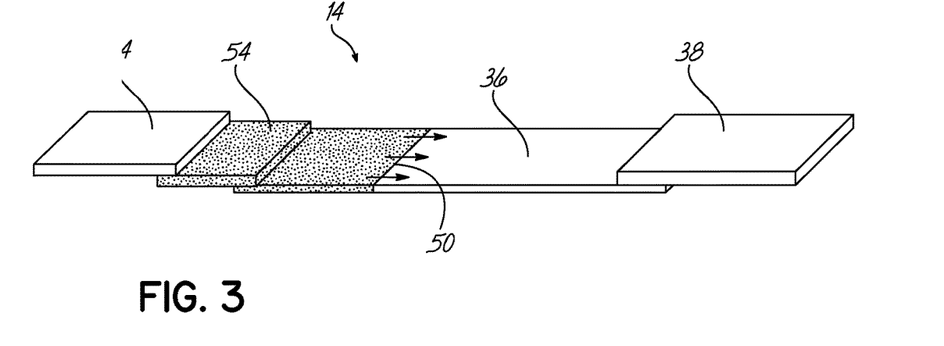
FIG. 3 is a perspective view of an alternative embodiment of an analytical membrane in accordance with embodiments of the invention.

An alternative embodiment, illustrated in FIG. 3, the analytical membrane 14 may further include a blood storage section 54 between the sample section 34 and the analytical section 36. A small sample of a subject's blood may be printed on the blood storage section 54, thereby allowing this embodiment of the device 10 to be used to evaluate the effect of compounds, such as drugs, chemicals, and other biological fluids, on a clotting property in the subject's blood. For example, a 1 μL sample of the subject's blood may be applied, such as by printing, to the blood storage section 54. Then a liquid sample that includes the compound of interest is applied to the sample section 34. Capillary forces will drive the compound sample through the stored blood sample and into the analytical membrane where the effect of the compound sample on a blood clotting property is evaluated. In an exemplary embodiment, blood storage section has the same width as the sample section 34 and the analytical section 36, but can have a length that varies depending on the volume of the subject's blood that is to be analyzed. For example, the blood storage section 54 may have a length that ranges between about 10 mm and about 20 mm and will overlap the adjacent sample and analytical sections 34, 36 by about 2 mm.

EXAMPLE 1

In this example, the use of an embodiment of the invention for detecting blood coagulation ability is described. Whole blood is a very rich medium, which is made up of approximately 45% by volume cells—erythrocytes (red blood cells—RBC), leukocytes (white blood cells—WBC) and platelets. More than 99% of cells in blood are RBCs. The remaining 55% of whole blood is protein-rich plasma, consisting of mostly water, with dissolved proteins, gas and ions. After an injury, human blood outside the vascular system clots within 2-6 min, following a sequential process (coagulation cascade) that is highly regulated by various proteins (coagulation factors) and critically depends on free $Ca^{2+}$ ions. Addition of sodium citrate to fresh whole blood binds $Ca^{2+}$ ions and, hence, prevents coagulation. In this example, non-coagulating citrated rabbit blood is the starting point for experiments. By adding various amounts of free $Ca^{2+}$ ions into citrated blood, the coagulation process is initiated and investigated under controlled conditions, thus being able to mimic blood coagulation properties in vitro.

Materials and Methods

Chemicals and Materials

Citrated rabbit whole blood (HemoStat Laboratories, Dixon, Calif.) was used as the substitute of human whole blood. According to the supplier, the volume ratio of rabbit whole blood to citrate solution [4% w/v trisodium citrate (Sigma-Aldrich) in water] is 4 to 1. This corresponds to significant amount of citrate beyond what is needed for $Ca^{2+}$ immobilization. Citrated rabbit plasma was obtained by centrifugation of the citrated rabbit whole blood (see Sec. Fibrintimer samples). Various concentrations (50 mM to 500 mM; 50 mM increment) of $CaCl_2$ (Fisher Scientific) aqueous solutions were added to citrated rabbit whole blood as coagulation activator to mimic fresh human whole blood. 0.9 wt. % NaCl (Fisher Scientific) aqueous solution was used for blood sample dilution. 6 wt. % 2000 kDa dextran (Sigma-Aldrich) aqueous solution was used as a comparison to citrated rabbit blood when testing the unique effect of $Ca^{2+}$ ions.

Millipore HF075 nitrocellulose membrane was used as analytical membrane in the analytical membrane on which blood coagulation took place. The HF075 membrane used in this study has a water flow rate of 0.5 mm/s, which is within the range specified by the manufacturer [75±19 s/4 cm (0.71 mm/s to 0.43 mm/s)]. The porosity of the various membranes in the exemplary inventive devices was measured using the water uptake method. The HF075 membrane has a porosity of 78.0%. Millipore G041 fiberglass membrane was used as sample pad due to its high porosity (~93%), through which plasma and blood cells can move easily. Millipore C048 cellulose paper, used as wicking pad to provide continuous capillary force, has a measured flow rate of 0.63 mm/s and a porosity of 72.3%. The pore size of nitrocellulose membranes used in the devices 10 ranges from 3-20 μm. While the diameter of RBCs is typically in the 6-8 μm range, they are highly deformable and are known to pass through membranes with pore diameter as small as 2.5-3 μm.

Exemplary Analytical Device

An analytical device in accordance with embodiments described herein and as shown in FIGS. 1-2B, the analytical device consists of a two-piece cassette that is designed to snap together. The top portion has a window that acts as a reservoir to contain sample liquid and a second window opening to observe fluid flow transport. In the example the blood sample was dispensed into the reservoir and then was automatically transported to the analytical membrane through capillary action. The analytical membrane consists of four components—sample section, analytical section, wicking section and membrane backing. The analytical membrane was placed inside alignment ridges of the cassette, with the sample section beneath the reservoir and at least a portion of the analytical section 36 visible through the observation window, as shown in FIGS. 1 and 2. This provided good alignment between analytical membrane and cassette, and good reproducibility of the analytical devices and experimental results.

During experiments, a blood sample was dispensed into the sample window, absorbed by the sample section, and then transported onto and through the analytical section. The cassette pieces were designed such that the wall of the dispensing reservoir was lightly pressed onto the sample section 34 when the cassette was snapped together. The blood sample soaked the sample section 34 and flowed onto the analytical section in a controlled manner. As whole blood flows through the analytical section, separation of RBCs from plasma occured with the plasma fraction moving much faster than the RBCs. This process is illustrated in FIG. 2A, where the top portion of the housing 12 forming the cassette is removed after a blood sample experiment is performed. In this particular experiment a small amount of whole blood was dispensed in order to show both the plasma and RBC fronts on the nitrocellulose membrane. In a typical 4-minute long experiment, the plasma reaches the wicking pad at an early stage of RBC transport, wetting the entire membrane and providing continuous capillary driving force during the measurement.

Sample Preparation

Analytical Device Samples—In experiments with embodiments of the inventive analytical device, 160 μL of citrated rabbit blood was added to 5 μL 0.9% NaCl solution, followed by adding 15 μL $CaCl_2$ solutions (50 mM to 500 mM; increment 50 mM). For the control experiments without $CaCl_2$ addition, 15 μL 0.9% NaCl solution was used as a substitute for the 15 μL $CaCl_2$ solution to maintain blood cell concentration constant in sample fluid for all cases. All solutions were pre-heated to 39° C. After each blood sample was made, it was incubated in the 39° C. water bath for an additional 2 min to initiate the blood coagulation process by providing an environment similar to rabbit's body. Immediately after the water bath, a volume of 100 μL from the overall sample was dispensed into the reservoir.

Fibrintimer Samples—For comparison to the experiments with the inventive device, a CoaData 2000 Fibrintimer® (American LAbor, Durham, N.C.) was used to determine the clotting time of plasma obtained by centrifugation of citrated whole rabbit blood samples. The clotting time measurement started from the moment of adding $CaCl_2$ solution as coagulation activator to the plasma and ended at the moment of detectable fibrin clot formation. The turbo-densitometric method utilized in the Fibrintimer® is a sensing method that combines stirring action and optical density measurement.

Plasma samples were obtained by centrifugation (Eppendorf MiniSpin, Germany) of citrated rabbit whole blood at 600 g for 10 min. A cuvette containing 80 μL of citrated rabbit plasma was placed into the reaction chamber first for incubation at 37° C. (fixed temperature in instrument). After 2 min, 100 μL of pre-mixed coagulation activating solution (15 μL $CaCl_2$ solution and 85 μL 0.9% NaCl solution) was added to the cuvette to initiate the coagulation process and the timer was started. CaCl$_2$ solution with several concentrations from 100 mM to 500 mM, in increments of 100 mM, was used. A 250 mM CaCl$_2$ solution was also included.

Results and Discussion

Measurements from Embodiment of Inventive Device

Figure 5:
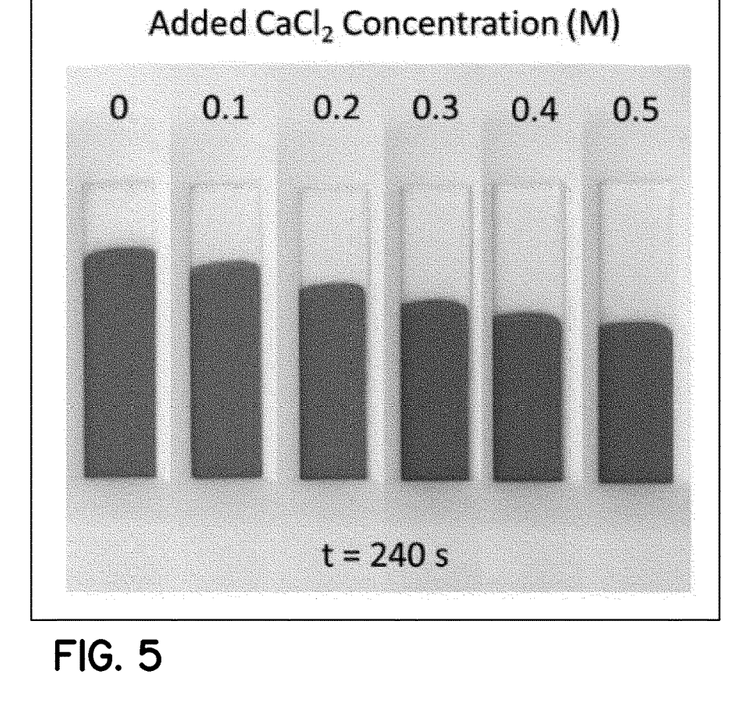
FIG. 5 is a photograph of citrated whole rabbit blood flow through a plurality of analytical membranes in the presence of increasing concentrations of the coagulation activator $CaCl_2$ after a duration of 240 seconds.

The progress of RBCs in the embodiment of the analytical devices is illustrated in the photographs of FIG. 5 as a function of added CaCl$_2$. The photographs were taken at 240 s after the moment when RBCs are just visible in the device window for the first time. From the photographs it can be clearly observed that RBC travel distance (over a fixed time) decreases with increasing CaCl$_2$ concentration. This confirms that the introduction of Ca$^{2+}$ ions from the added CaCl$_2$ solution affects the blood coagulation process in the Exemplary inventive device and that the overall process has the potential to be used as a guide for blood coagulation screening and diagnosis.

Figure 6:
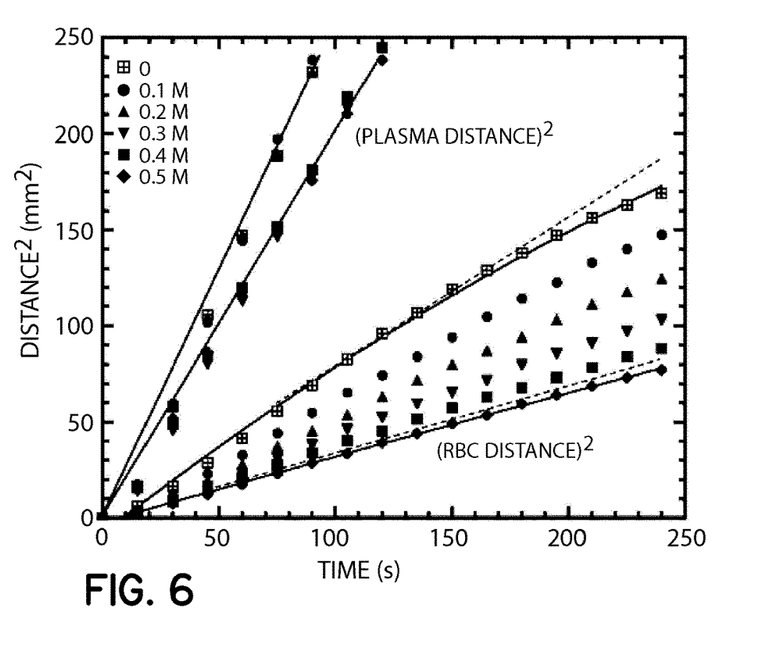
FIG. 6 is a graph of data showing the square of the distance traveled per unit time of citrated whole rabbit blood and corresponding plasma fraction in the presence of increasing concentrations of the coagulation activator $CaCl_2$ through an analytical membrane in an embodiment of a blood property analytical device in accordance with embodiments of the invention.

FIG. 6 shows the relationship between the distance that blood samples travelled and their corresponding travel time through the nitrocellulose membrane in the Exemplary inventive device when CaCl$_2$ solutions with various concentrations (0 to 500 mM) were added. In FIG. 6, the (travel distance) vs. time for the plasma and RBC fronts are plotted on a linear scale. The plasma component travels much faster than the RBCs, reaching the end of the observation window (coincident with the edge of the wicking pad) in 90 s (for low or no added Ca$^{2+}$ concentrations) to 120 s (for high added Ca$^{2+}$ concentration). The data on FIG. 6 demonstrates that the flow of blood through the analytical membrane obeys the Washburn equation. As expected, the RBC flow rate was significantly slower and more strongly affected by the addition of Ca$^{2+}$ ions. The RBC front did not reach the wicking pad in any of the samples, even in the absence of added Ca$^{2+}$ ions. It was apparent that both blood components follow fairly closely the Washburn equation. The reduction in the slope of the measured travel distance with time for samples with increasing CaCl$_2$ concentration is related to the time derivative of the Washburn equation, which is proportional to the ratio of the surface tension to viscosity. As the added Ca$^{2+}$ ion concentration increased, the resulting enhancement in the coagulation process increased the effective viscosity of both plasma and RBC components of the blood sample. The deviation from agreement with pure Washburn flow (shown by the dashed lines) starts at a flow time of ~120-130 s and was most pronounced for samples where the RBC flow distance was the longest, namely the sample with no CaCl$_2$ added. Since the experiment used a limited fluid volume, this effect was probably due to the evaporation of the plasma that occurs for longer times and distances, which in turn affect the capillary force present.

It is important to point out that for plasma transport in whole blood samples with different concentrations of added CaCl$_2$, the effect of Ca$^{2+}$ ions on plasma flow was fairly small. Unlike what was observed from RBC transport, plasma flow rate did not decrease significantly when more Ca$^{2+}$ ions were added. This demonstrates that RBCs are necessary to visualize the coagulation process in the plasma during which fibrin threads are gradually formed throughout the membrane, thus significantly slowing down the movement of RBCs.

Figure 7:
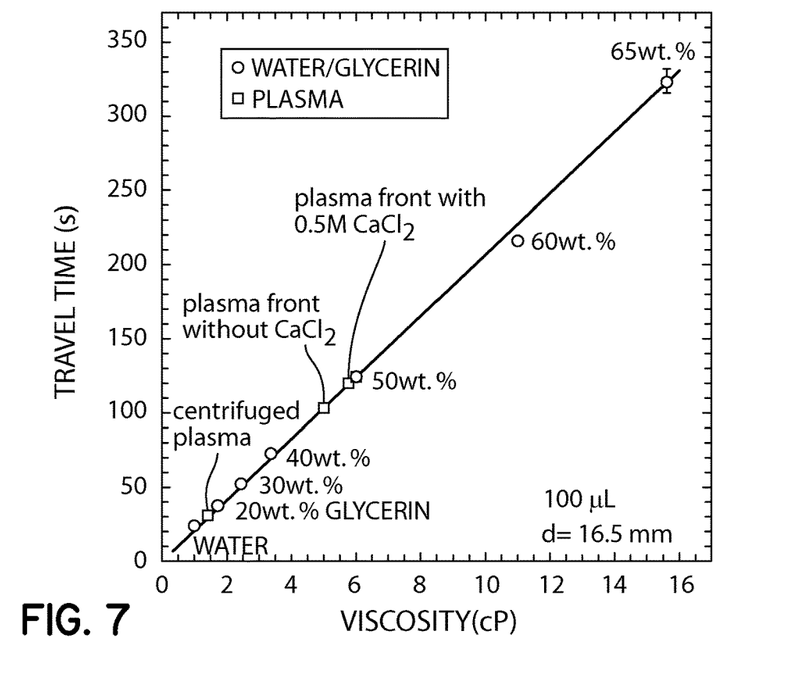
FIG. 7 is a graph of travel time of samples with different viscosities through the analytical membrane of an analytical device in accordance with embodiments of the invention.
Figure 8:
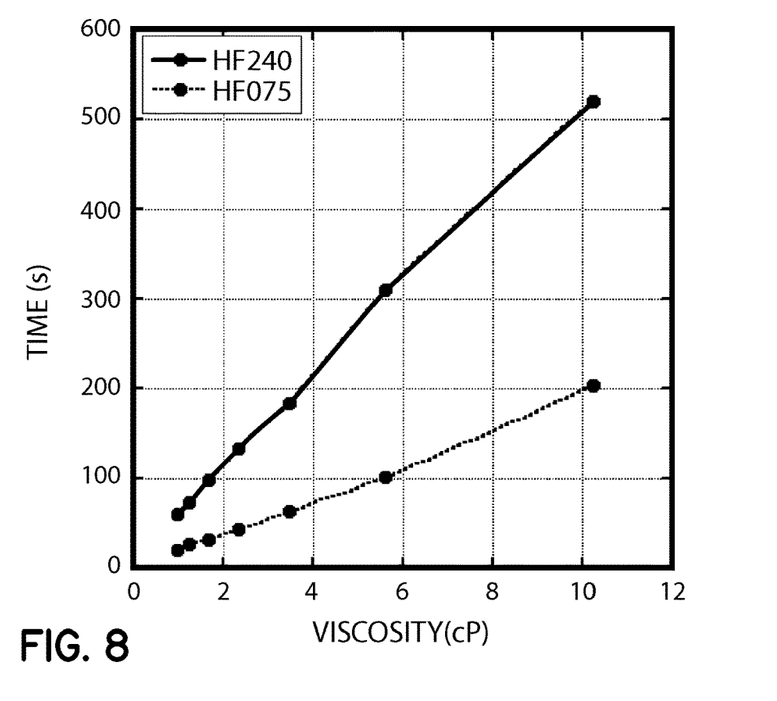
FIG. 8 is a graph of travel time of samples of different viscosities for two analytical membranes of different flow rates of an analytical device in accordance with embodiments of the invention.

As discussed above, the travel time of biological fluids in the exemplary devices was strongly affected by their viscosity. Once the relationship between the viscosity and the travel time of liquids is established in an exemplary device, one can determine the viscosity of sample fluids based on their travel time in the exemplary device. To accomplish this in the case of blood plasma, solutions of glycerin and water have been utilized. Glycerin/water mixtures with up to 65 wt. % glycerin have an increase in viscosity of up to ~15× compared to plain water (~1 cP), while their surface tension exhibits only a negligible variation (~5%). Travel times of mixtures were measured until the liquid front reached a distance of 15.8 mm from the starting location. The travel times of several glycerin/water mixtures (from 0 to 65 wt. %) and their corresponding viscosities are shown in FIG. 7 (circles). Interestingly, these results provide a linear relationship between travel time and the viscosity of the liquid, establishing the linear equation also shown in FIG. 7. Furthermore, the slope of the linear relationship can be adjusted by selecting analytical membranes of different lengths or flow speeds. For example, denser membranes (e.g. HF240) with slower flow rate than HF075 result in a larger time change with viscosity, thus providing higher resolution in the low viscosity range (FIG. 8). These results demonstrate that the inventive devices can provide sufficient resolution to detect a small variation of blood/plasma viscosity, such as those found in certain medical conditions.

Based on the linear relationship developed for glycerin/water mixtures, the viscosities of plasma with different CaCl$_2$ concentrations (squares) can be obtained using their respective travel time (from FIG. 6). The effective viscosity values calculated for plasma separated from the whole blood within the exemplary devices are ~5.0 cP for the case of no added CaCl$_2$ and ~5.8 cP when 500 mM CaCl$_2$ was added. The viscosity value calculated for pure plasma on the exemplary devices (obtained by centrifugation) is significantly lower (~1.4 cP) because there is no interaction with blood cells.

To verify the exclusive effect of Ca$^{2+}$ ions on citrated blood transport, similar experiments were conducted with dextran samples to which CaCl$_2$ solutions were added. Dextran is a polysaccharide that is used in solution to act as a replacement for blood plasma in cases of severe blood loss. The dextran solution utilized in these experiments had a viscosity of ~7.7 cP (measured using a falling-ball viscometer), which is in the range of anti-coagulated rabbit blood. Except for using dextran solution instead of citrated blood, the other experimental conditions remained the same.

Figure 9:
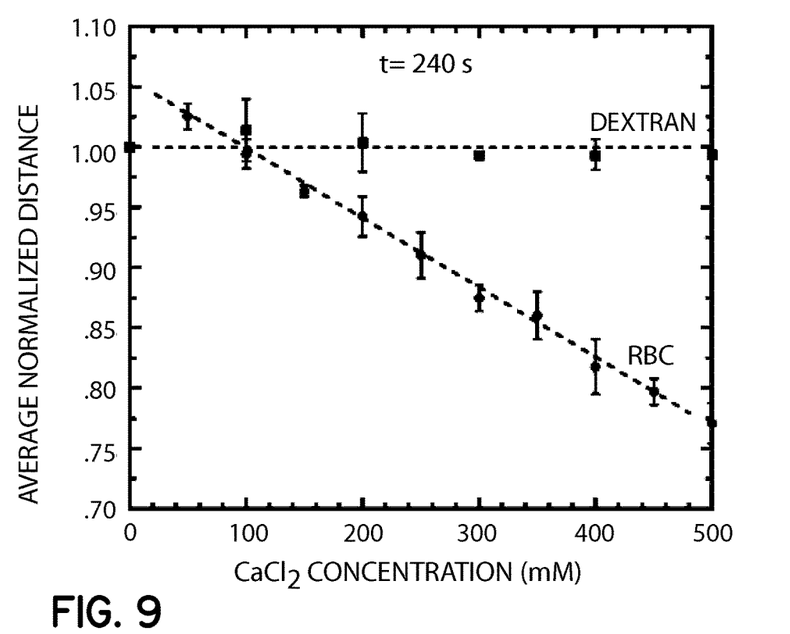
FIG. 9 is a graph demonstrating the average normalized distance citrated whole rabbit blood or Dextran flows through an analytical membrane in the presence of increasing concentrations of coagulation activator $CaCl_2$ after a duration of 240 seconds.

FIG. 9 contains data from whole blood transport experiments in the exemplary devices as a function of added CaCl$_2$ concentration for a duration of 240 s. Companion dextran based experiments are included for comparison. A linear decrease in the normalized RBC travel distance with increasing CaCl$_2$ solution concentration was observed, which was consistent with FIG. 5. Agreements with ideal linearity for the three sets of data are 0.9782, 0.98461 and 0.98401, indicating good reproducibility of the experiments. FIG. 9 also clearly shows that the travel distance of the dextran solution is independent of the CaCl$_2$ additive. This demonstrates that Ca$^{2+}$ ions only alter the viscosity of the blood samples and not that of substitute fluids. Data range bars are introduced in this figure to cover all three values of the repeated sets of experiments for both citrated rabbit blood and dextran solution. FIG. 9 illustrates the normalized distance travelled at 240 s for RBCs in whole blood samples and for dextran solutions.

Figure 10:
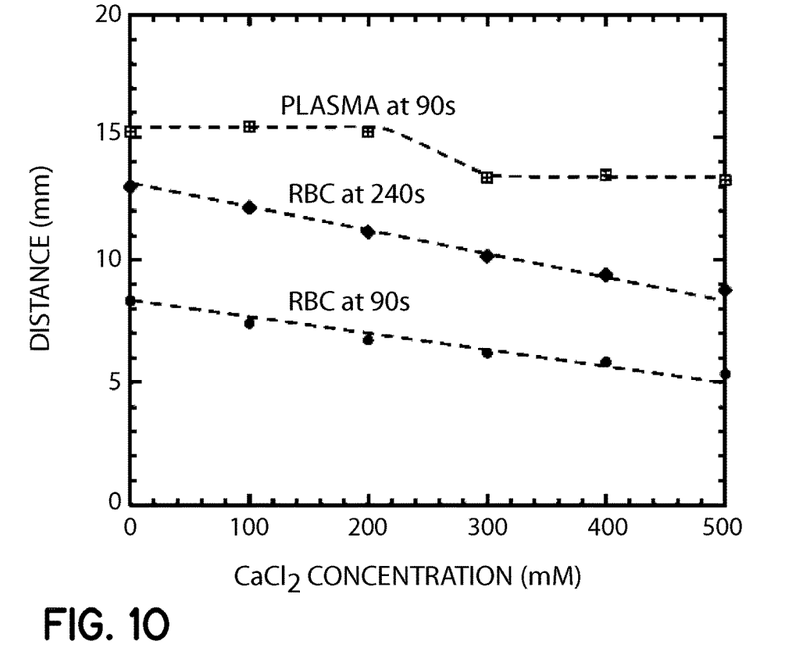
FIG. 10 is a graph of distance travelled by RBCs at 90 s and 240 s and the distance travelled by plasma at 90 s when each of the samples was in the presence of increasing concentrations of $CaCl_2$.

FIG. 10 compares the travel of plasma vs. RBCs for travel times of 90 and 240 s. The plasma travel distance after 90 s for samples with added CaCl$_2$ solution concentrations from 0 to 500 mM is essentially constant, with only a slight decrease in distance between 200 and 300 mM. By contrast, RBC transport distance at both 90 and 240 s showed a monotonic decrease with increasing CaCl$_2$ concentration. The straight-line slope indicates that the RBC transport characteristics can eventually provide a quantitative, as well as qualitative, method of blood coagulation analysis.

Clotting Time Measurements

Figure 11:
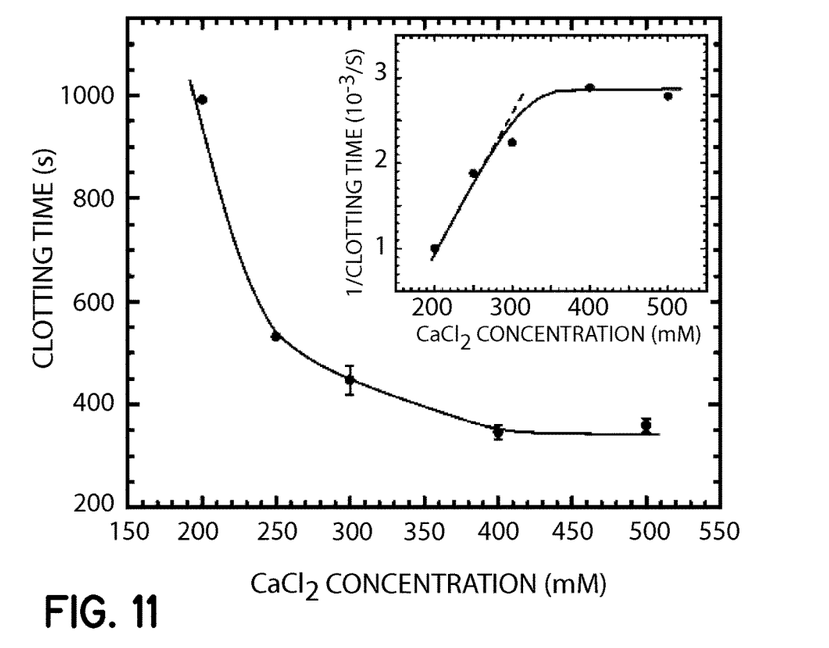
FIG. 11 is a graph of clotting times in samples obtained with a CoaData 2000 Fibrintimer device.

Measurements of clotting time in plasma samples centrifuged from citrated whole blood were performed using the CoaData 2000 Fibrintimer®. FIG. 11 shows the plasma clotting time as a function of $CaCl_2$ solution concentration. Experiments were repeated 3 times to confirm reproducibility. No fibrin clot formation is detected when 100 mM $CaCl_2$ solution was added, which was probably due to insufficient amount of $Ca^{2+}$ ions to form a fibrin clot. As shown in FIG. 11, the clotting time decreased monotonically from ~1,000 s for a $CaCl_2$ solution concentration of 200 mM to a minimum level of ~350 s for $CaCl_2$ solution concentration of 400-500 mM. The inset in FIG. 11 shows the relationship between the inverse of clotting time and the added $CaCl_2$ concentration. The relationship is linear for low $CaCl_2$ concentration up to 300 mM, and gradually reaches a plateau at ~400 mM. It is interesting to point out the similarity between the clotting time of citrated rabbit plasma as a function of $CaCl_2$ solution concentration shown in FIG. 11 and corresponding results reported for the clotting time of citrated human plasma vs. free $Ca^{2+}$ ions within the plasma.

Figure 12:
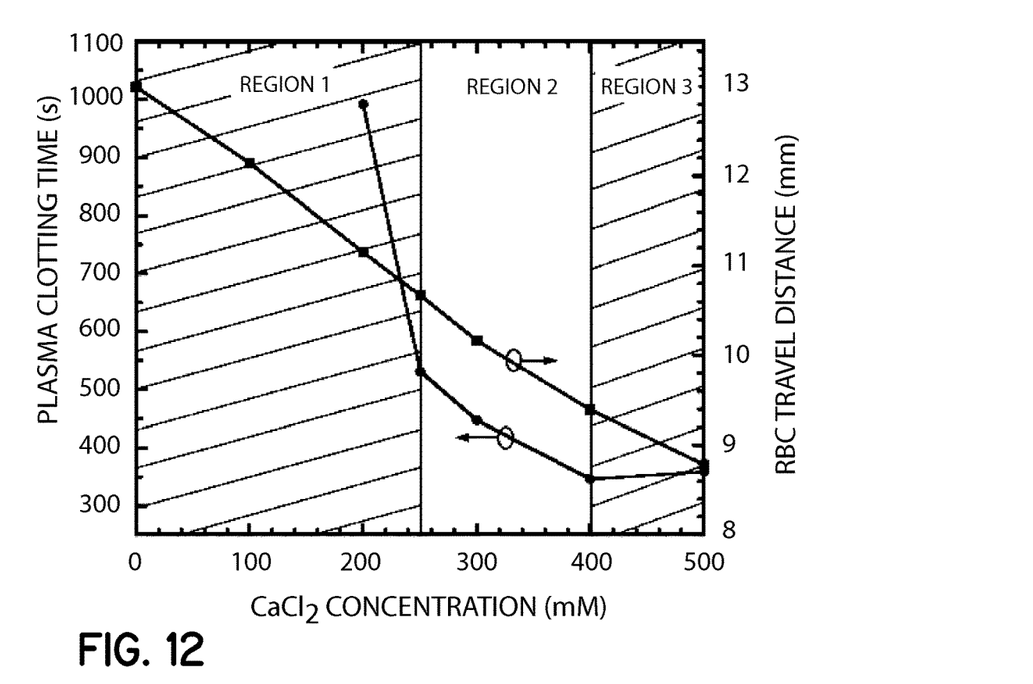
FIG. 12 is a graph comparing clotting time data obtained with CoaData 2000 Fibrintimer device with travel time data obtained with an exemplary embodiment of the invention.

It is instructive to compare the results obtained with RBC transport in the exemplary inventive devices and plasma clotting results obtained with the CoaData 2000 Fibrintimer®. FIG. 12 contains the RBC travel distance in Exemplary inventive devices and the plasma clotting times as a function of the concentration of added $CaCl_2$ solutions. For ease of comparison, three regions have been identified in the graph contained in FIG. 12. The RBC travel time is fixed at 240 s for all samples and the Fibrintimer® has a maximum detectable clotting time of 1,000 s (~16 min).

Region 1 covers the addition of relatively low $CaCl_2$ concentration solutions, from none to 250 mM. At these low concentrations a relatively small number of $Ca^{2+}$ ions is added into the blood and plasma samples, therefore the coagulation effect is relatively weak. The plasma clotting time exceeds the Fibrintimer® limit until a 200 mM $CaCl_2$ solution is used, after which a sharp decrease in clotting time at 250 mM is observed. On the other hand, the RBC travel distance on the exemplary inventive devices displays a straight-line decrease with $CaCl_2$ concentration over the 0 to 250 mM range. Unlike plasma clotting measurements that only detect the effective end point of the coagulation process and which can be quite lengthy in the case of low/very low $Ca^{2+}$ ion concentration exceeding the time limit of available instruments, exemplary inventive device-based measurements experience the whole blood coagulation process on the analytical membrane in a matter of ~100-200 s. This makes the exemplary inventive device more sensitive to slight changes in coagulation ability that can be difficult to detect using the plasma clotting method. In Region 2, both plasma clotting time and the RBC travel time display a straight-line decrease with increasing $CaCl_2$ solution concentration. Detection abilities of both approaches appear comparable in Region 2. Finally, in Region 3 that covers higher $CaCl_2$ solution concentrations (400-500 mM), while the measured clotting time becomes more or less constant at a value of ~350 s, the exemplary inventive device continues to provide a straight-line relationship.

These data demonstrate that the liquid flow approach provides a wider detection range with a linear response for coagulation diagnosis than that of conventional plasma clotting measurements.

EXAMPLE 2

Figure 13:
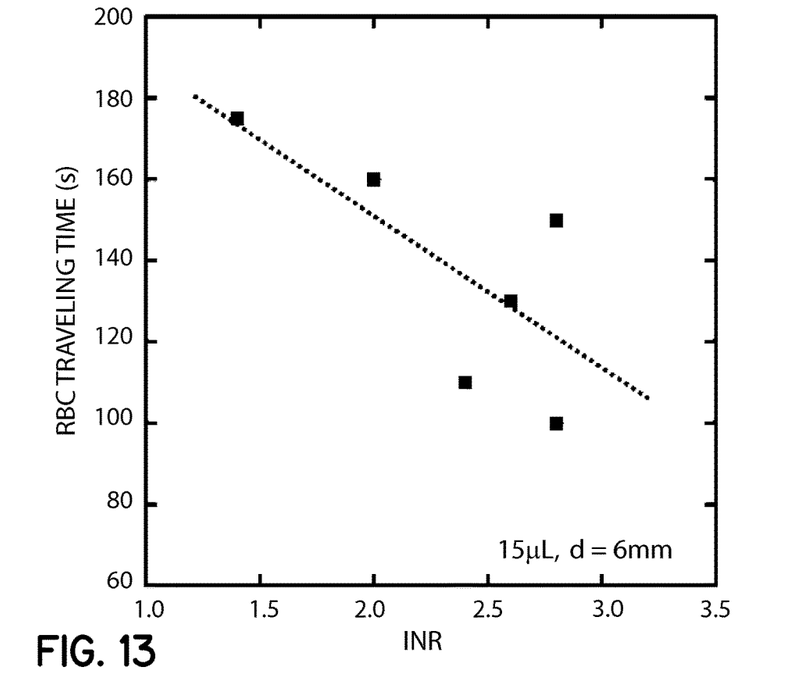
FIG. 13 is a graph comparing human INR data collected from several individuals with RBC travel time from corresponding clinical blood samples through the analytical membrane of an exemplary embodiment of the device.

In this example, blood samples were collected from human subjects treated with oral anticoagulants and analyzed with exemplary inventive devices as described in Example 1. Whole blood samples were collected by a trained health care professional. After pricking the subject's finger, blood was collected in a capillary tube and quickly transferred to the reservoir of an exemplary inventive device. The exemplary inventive device was quickly (within a few seconds) placed in view of a camera on a mobile device that was supported by a stand similar to that shown in FIG. 4. The mobile device was installed a software programmed to capture images of the analytical membrane using the camera at pre-established times. The images were analyzed to determine the time point when the RBCs had travelled a distance of 6 mm. International Normalized Ratio of prothrombin time (INR) data were also collected with blood samples from the same subjects. FIG. 13 plots the RBC travel time against the INR data for each subject. The data show that blood samples having a high INR (i.e., less viscous and a slower clotting time) travel faster than samples having a lower INR. These demonstrate that embodiments of the inventive device may be used to monitor blood clotting properties in subjects.

EXAMPLE 3

Figure 14:
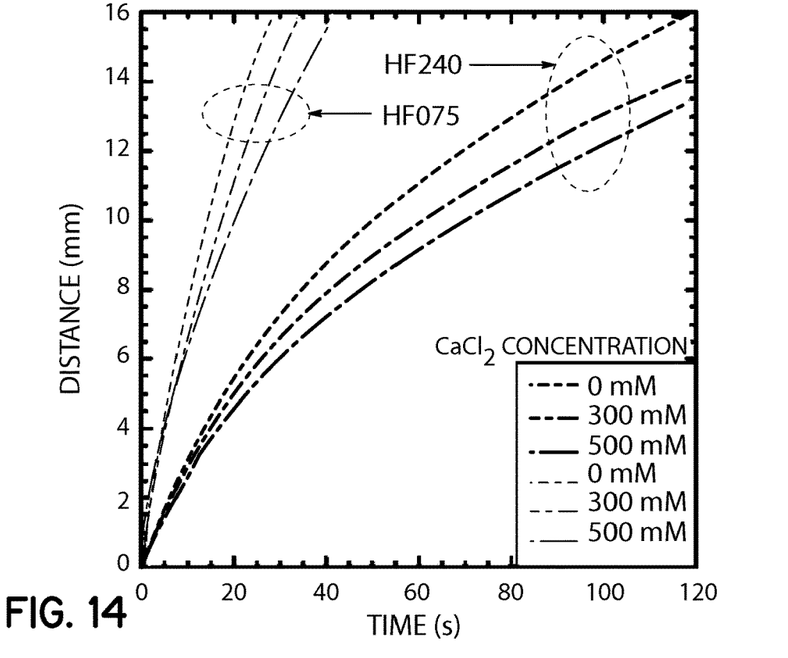
FIG. 14 is a graph of blood travel distance vs time for different concentrations of $CaCl_2$ on two membranes of different density obtained with an alternative embodiment of the invention that includes a blood printed in accordance with embodiments of the invention.

In this example, alternative embodiments of the inventive device having a blood storage section was evaluated. Approximately 1 μL of blood was printed onto the blood storage section for each device. The first alternative exemplary device utilized the Millipore HF075 nitrocellulose membrane for the analytical section utilized in the Examples 1 and 2. The second alternative exemplary device utilized the more dense nitcrocellulose membrane from Millipore HF240 for the analytical section. Liquid samples containing either no $CaCl_2$, 300 mM $CaCl_2$ or 500 mM $CaCl_2$ were applied to the reservoir of the exemplary devices and the distance travelled by the RBCs was monitored for a duration of up to about 120 s. As shown in FIG. 14, the alternative embodiments were capable of detecting the increased clotting that occurs in blood samples as a result of the increased concentration of calcium ions in the liquid sample. Moreover, the data also demonstrate that increasing the density of the analytical section decreases the speed with which the sample travels through the analytical section.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described. Accordingly, departures may be made from such details without departing from the scope or spirit of the general inventive concept.

What is claimed is:

1. A device for analyzing a blood coagulation property in a blood sample comprising a housing having an analytical membrane partially enclosed in a housing, said analytical membrane including a porous hydrophilic sample portion, a porous hydrophilic analytical portion and a porous hydrophilic wicking portion, wherein said analytical portion has a porosity that differs from said sample portion and said analytical membrane does not include any additional reagents or pretreatments.

2. The device of claim 1 wherein said sample portion has a porosity of at least 90%.

3. The device of claim 1 wherein said sample portion is formed from a material selected from the group consisting of fiberglass and polyester.

4. The device of claim 1 wherein said analytical portion has a porosity in a range from about 70% to about 90%.

5. The device of claim 1 wherein the analytical portion has a flow rate of water ranging between about 0.1 mm/s and about 1 mm/s.

6. The device of claim 1 wherein the analytical portion has a flow rate of water ranging between about 0.4 mm/s and about 0.6 mm/s.

7. The device of claim 1 wherein the analytical portion has a flow rate of water ranging between about 0.5 mm/s and about 0.55 mm/s.

8. The device of claim 1 wherein the analytical portion is formed from a material having an affinity to bind proteins and a color that visually contrasts with red blood cells.

9. The device of claim 1 wherein the analytical portion is formed from a nitrocellulose membrane.

10. The device of claim 1 wherein at least one of the sample portion, the analytical portion, and the wicking portion includes a non-porous substrate on a top or bottom surface.

11. The device of claim 1 wherein the device is capable of analyzing a sample having a volume ranging between about 15 µl and about 150 µl.

12. The device of claim 1 wherein the device is capable of analyzing a sample having a volume ranging between about 20 µl and about 60 µl.

13. The device of claim 1 wherein the wicking portion is capable of absorbing at least the volume of liquid in a sample before becoming saturated.

14. The device of claim 1 wherein the sample portion, the analytical portion, and the wicking portion are each formed from a separate section of membrane and a proximal end of the analytical portion overlaps with a distal end of the sample portion and a distal end of the analytical portion overlaps with a proximal end of the wicking portion.

15. The device of claim 1 further comprising a blood storage portion between the sample portion and the analytical portion.

16. The device of claim 1 wherein said housing includes an observation window through which at least a portion of the analytical membrane may be observed.

17. The device of claim 16 wherein said housing further includes markings indicating the results of the analysis.

18. A kit for analyzing a blood coagulation property in a blood sample comprising:
a blood coagulation property analytical device in accordance with claim 1, and
a stand configured to hold an image capturing device in a position so that the blood coagulation property analytical device is in the field of view of the image capturing device.

19. The kit of claim 18 further comprising a software code for analyzing an image of the blood coagulation property analytical device capture by the image capturing device.

20. The kit of claim 19 wherein the software code is capable of performing at least one of identifying a red blood cell leading edge, calculating the distance travelled by a red blood cell leading edge, comparing the distance travelled by a red blood cell leading edge against stored data, making a determination if the distance travelled by a red blood cell leading edge indicates a safe or unsafe condition with respect to the blood coagulation property, correlating the distance travelled by a red blood cell leading edge into an equivalent blood coagulation value from a different analytical method, forwarding data about the image to a health care provider, and alerting at least one of a user or a health care provider if the distance travelled by a red blood cell leading edge indicates an unsafe condition.

21. A method of analyzing a blood coagulation property in a blood sample comprising:
obtaining a blood sample from a subject;
applying the blood sample to the sample portion of a blood coagulation property analytical device in accordance with claim 1, and
identifying the location of a red blood cell leading edge after a predetermined period of time.

22. The method of claim 21 further comprising correlating the location of the red blood cell leading edge with a condition.

23. The method of claim 21 wherein said duration of time ranges from about 1 minute to about 10 minutes.

24. The method of claim 23 wherein said duration of time ranges between about 2 minutes and about 5 minutes.

25. The method of claim 21 wherein the duration of time is sufficient for a leading edge of red blood cells to travel a distance ranging from about 10 mm to about 50 mm.

26. The method of claim 21 wherein the duration of time is sufficient for a leading edge of red blood cells to travel a distance ranging from about 10 mm to about 20 mm.

* * * * *

UNITED STATES PATENT AND TRADEMARK OFFICE
CERTIFICATE OF CORRECTION

PATENT NO. : 10,488,424 B2
APPLICATION NO. : 15/122674
DATED : November 26, 2019
INVENTOR(S) : Andrew J. Steckl et al.

It is certified that error appears in the above-identified patent and that said Letters Patent is hereby corrected as shown below:

In the Specification

Column 1, Line 6, "Present" should be --present--.

Column 2, Lines 35-37, "FIG. 2B is longitudinal cross-section side view of the device of FIG. 2A taken along lines 3-3;" should be --"FIG. 2B is a longitudinal cross-section side view of the device of FIG. 2A taken along line 3-3;"--.

Column 6, Line 46, "An alternative embodiment," should be --In an alternative embodiment,--.

Column 8, Line 52, "LAbor," should be --Labor,--.

Column 9, Line 15, "Exemplary" should be --exemplary--.

Column 11, Line 26, "Exemplary" should be --exemplary--.

Column 12, Line 9, "was installed a software" should be --was installed with software--.

Column 12, Line 26, "was" should be --were--.

In the Claims

Column 14, Line 11 (Claim 19), "capture" should be --captured--.

Signed and Sealed this
Twenty-sixth Day of May, 2020

Andrei Iancu
*Director of the United States Patent and Trademark Office*